(12) United States Patent
Tixier et al.

(10) Patent No.: US 8,314,388 B2
(45) Date of Patent: Nov. 20, 2012

(54) SINGLE-SIDED INFRARED SENSOR FOR THICKNESS OR WEIGHT MEASUREMENT OF PRODUCTS CONTAINING A REFLECTIVE LAYER

(75) Inventors: Sebastien Tixier, North Vancouver (CA); Frank Martin Haran, North Vancouver (CA)

(73) Assignee: Honeywell ASCa Inc., Mississauga (CA)

( * ) Notice: Subject to any disclaimer, the term of this patent is extended or adjusted under 35 U.S.C. 154(b) by 60 days.

(21) Appl. No.: 12/973,859

(22) Filed: Dec. 20, 2010

(65) Prior Publication Data

US 2012/0153149 A1 Jun. 21, 2012

(51) Int. Cl.
*G01J 5/00* (2006.01)
(52) U.S. Cl. .................................................. 250/338.1
(58) Field of Classification Search .... 250/338.1–338.5, 250/339.01–339.15, 340, 341.1–341.8, 342–353
See application file for complete search history.

(56) References Cited

U.S. PATENT DOCUMENTS

| | | | |
|---|---|---|---|
| 3,793,524 A | 2/1974 | Howarth | |
| 4,129,781 A * | 12/1978 | Doyle | 250/341.3 |
| 4,311,658 A | 1/1982 | Nicoll | |
| 4,403,010 A | 9/1983 | Festag | |
| 4,582,431 A | 4/1986 | Feldman | |
| 4,797,246 A | 1/1989 | Reinke | |
| 4,957,770 A | 9/1990 | Howarth | |
| 5,230,923 A | 7/1993 | Hirokawa | |
| 5,276,327 A * | 1/1994 | Bossen et al. | 250/339.09 |
| 5,391,891 A * | 2/1995 | Wiegleb et al. | 250/574 |
| 5,455,422 A * | 10/1995 | Anderson et al. | 250/341.1 |
| 5,795,394 A | 8/1998 | Belotserkovsky | |
| 5,914,490 A * | 6/1999 | Sumen et al. | 250/339.11 |
| 6,074,483 A | 6/2000 | Belotserkovsky | |
| 6,179,918 B1 | 1/2001 | Belotserkovsky | |
| 6,183,561 B1 | 2/2001 | Belotserkovsky | |
| 6,565,343 B1 | 5/2003 | Krycki | |
| 6,793,854 B1 | 9/2004 | Kirjavainen | |
| 6,805,899 B2 | 10/2004 | MacHattie | |
| 6,848,795 B2 | 2/2005 | Kaminsky | |
| 7,145,147 B1 * | 12/2006 | Shelley et al. | 250/339.11 |
| 7,223,977 B2 | 5/2007 | Shelly | |
| 7,291,856 B2 | 11/2007 | Haran | |
| 7,321,425 B2 | 1/2008 | Haran | |
| 7,382,456 B2 | 6/2008 | Tixier | |
| 7,436,469 B2 | 10/2008 | Gehlsen | |
| 7,452,356 B2 | 11/2008 | Grove | |
| 7,763,876 B2 | 7/2010 | Banton | |

FOREIGN PATENT DOCUMENTS

| | | |
|---|---|---|
| JP | 1203911 A | 8/1989 |
| JP | 5066114 A | 3/1993 |

OTHER PUBLICATIONS

JP 5066114A English Abstract, ESPACENET.
JP 1203911A English Abstract, ESPACENET.
Search Report for PCT/CA2011/001379, Mar. 13, 2012.

* cited by examiner

*Primary Examiner* — Kiho Kim
(74) *Attorney, Agent, or Firm* — Cascio Schmoyer & Zervas

(57) ABSTRACT

An optical, non-contact sensor for measuring the thickness or weight of layered products and particularly those that contain a light-reflective substrate incorporates a reflective surface to cause incident radiation from a light source to plurality of time within the layered products before being detected in a receiver. A diffusing element can be incorporated as a diffuse source of illumination. The Lambertian-type light scattering generated by the diffuse element causes the incident light to interact multiple times with the layered product resulting in enhanced sensor sensitivity to selected components in the layered product and measurement error induced by specular reflection of the light from the reflective substrate is minimized.

19 Claims, 3 Drawing Sheets

SINGLE-SIDED INFRARED SENSOR FOR THICKNESS OR WEIGHT MEASUREMENT OF PRODUCTS CONTAINING A REFLECTIVE LAYER

FIELD OF THE INVENTION

The present invention generally relates to a system for measuring properties of sheet materials and especially of a layer of material that is formed on a reflective substrate and, more particularly, to an optical sensor that incorporates a reflective member on its operative surface to cause incident radiation from the sensor light source to be reflected a plurality of times within the layer of material product before being detected by the sensor receiver. The sensor can include a light diffusing element to diffuse or scatter the reflected light in order increase the number of times the light interacts with the components in the layer of material and therefore increase the sensitivity of the sensor.

BACKGROUND OF THE INVENTION

In the manufacture of sheet materials, it is well known that various sheet properties can be detected "on-line," that is, while a sheet making machine is operating. On-line measurement devices measure sheet properties such as thickness, basis weight, moisture content, chemical composition and the like. Typically, such on-line devices employ sensors that periodically traverse, or scan, the moving sheets in the cross direction (CD), which is perpendicular to the machine direction (MD) of sheet travel. Depending upon the particular sheetmaking machine, cross-directional distances can range from about 10 to 12 meters and longer.

U.S. Pat. No. 4,957,770 to Howarth describes an infrared sensor to determine the amount of a coating material on a substrate using measurements of radiation reflected from a substrate or the transmission of radiation through the substrate, at two or more separate wavelength regions of infrared radiation. The infrared sensor includes an infrared source that transmits a beam of radiation toward the coated substrate such as a moving sheet of paper. When the beam reaches the sheet, it first passes through the coating material and then into the base paper sheet. A portion of the infrared energy is transmitted through the sheet while some of the infrared energy is reflected back in the general direction of the infrared source. In the case where the sensor is configured so that both the infrared source and receiver are positioned on the same side of the moving sheet of paper, the receiver measures the intensity of the reflected portion of the beam.

As is apparent, these standard single-sided sensors for measuring coat weight and other characteristics on layered products are configured for near normal diffusion scattering geometry that requires the product being measured to scatter light significantly so that a signal can be detected and analyzed. These single sided sensors are not especially suited for measuring thickness and weight of a coating that is formed on a reflective substrate.

SUMMARY OF THE INVENTION

The present invention is directed to an optical, non-contact sensor for measuring the thickness, weight and other physical characteristics of layered materials, especially of layered products that are formed on light reflective substrates. The invention is based in part on the recognition that the optical geometry of prior art single-sided infrared sensors limits the accuracy of coat weight measurements when the coating is formed on a reflective substrate such as in the case of plastic coated metal foils. In particular, with prior art sensor designs, the incident light from the light source of the sensor reflects primarily in the specular direction. Consequently, prior art measurements are extremely sensitive to the surface finish of the reflective substrate, the orientation of the layered product with respect on the sensor, and the distance between the layered product and the sensor.

The inventive sensor eliminates these constraints by positioning a reflective member, such as a specular mirror, between the main body of the sensor and the sensor radiation source and sensor radiation receiver so that incident radiation from the radiation source propagates through the layer of material being monitored. In a particularly preferred embodiment, a diffusing element is positioned between the reflective member and the layer of material. The diffusing element, along with the light source, functions as a diffuse source of illumination as light that travels toward the detector in the machine direction. The Lambertian-type light scattering generated by the diffusing element affords many benefits. Because the light interacts multiple times with the layer(s) of material, the sensor's sensitivity to selected components within the layer is enhanced. Finally, Lambertian-type light scattering ensures that the angular information is lost which minimizes the negative effect of specular reflection from the reflective substrate, which is associated with the layer of material, on sensor accuracy.

Accordingly, in one aspect, the invention is directed to an apparatus for sensing a layer of material that includes:

a housing, having an operative surface;

a radiation source, disposed within the housing, that directs a beam of incident radiation away from the operative surface and into a layer of material;

a radiation receiver, disposed within the housing, that detects at least a portion of a reflected beam that propagates through the layer of material; and means for causing radiation to be reflected through the layer of material a plurality of times before being detected by the radiation receiver.

In another aspect, the invention is directed to a single-sided infrared sensor, for measuring the thickness or weight of a sheet product moving in the machine direction, that includes:

a housing supporting a radiation source and a radiation receiver, wherein the radiation source directs a beam of incident infrared radiation into the sheet product; and reflective means disposed between the radiation source and the radiation receiver for reflecting radiation toward the sheet product such that radiation is reflected through the sheet product a plurality of times before reaching the radiation detector and the radiation propagates through the sheet product in the machine direction.

In yet another aspect, the invention is directed to a method of measuring a characteristic of a layer of material that is moving along a path that includes the steps of:

(a) directing radiation from a radiation source that is disposed on a first side of the path and into the layer of material; and (b) causing radiation to be reflected a plurality of times within the layer of material before being detected by a radiation receiver that is also disposed on the first side of the path.

DETAILED DESCRIPTION OF PREFERRED EMBODIMENTS

Figure 1A:
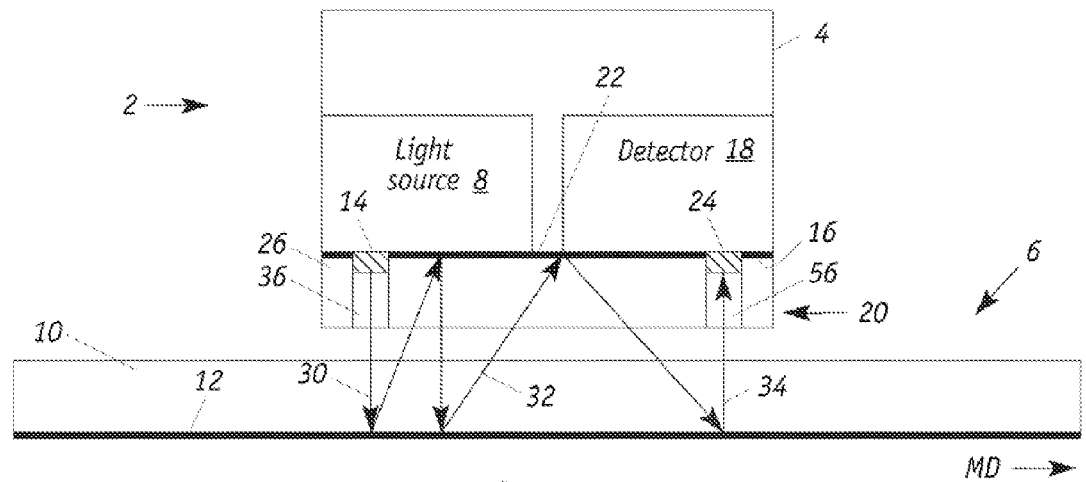
FIGS. 1A and 1B depict embodiments of the single-sided sensor of the present invention.

FIG. 1A illustrates a non-contacting optical sensor 2 that includes an enclosure 4 (also called "scanner head" or "head") that houses sensor components for measuring qualities, characteristics or features of a moving web 6. Layered materials that can be monitored include, but are not limited to, single and multi-layered compositions, coatings, films, webs or sheets. While the sensor will be illustrated in measuring characteristics in paper and plastic, it is understood that the sensor can be employed to detect a variety of components in a number of different materials including, for example, coated materials, fabrics, and the like. Sensor 2 is particularly suited for measuring the thickness or weight of a layer of material 10 that is a coated on a reflective laminant substrate 12. Sensor 2 includes a light source 8 and a receiver or detector 18 that are positioned in head 4. A reflective assembly 20, which is secured to the lower operative surface 22 of head 4, comprises a reflective member 16, such as a specular mirror. Preferably, it is covered by a clear protective layer 26, which is made of any suitable material, such as glass or plastic, which is transparent or translucent.

Apertures 36 and 56 provide access to light source 8 and detector 18, respectively. Lens 14 is positioned to focus a beam of incident radiation 30 through aperture 36 toward moving web 6 and lens 24 is positioned to collect radiation 34 that is reflected from reflective laminant substrate 12 of moving web 6 through aperture 56. Since light source 8 and detector 18 are arranged on the same side of the moving web 6, single-sided sensor 2 operates in the reflective mode. Light source 8 can comprise, for instance, an incandescent lamp to irradiate the coated substrate with radiation having wavelengths in at least first and second separate wavelength regions of the electromagnetic spectrum that are referred to as reference and measurement wavelength bands further described herein. As illustrated in FIG. 1A, sensor 2 is positioned so that light source 8 and receiver 18 define an axis that is preferably aligned along the machine direction (MD) of moving web 6.

With this configuration of the single-sided sensor, incident light 30 from light source 8 is reflected by reflective laminant substrate 12 and upper reflective member 16 multiple times before receiver 18 detects the light. By positioning sensor 2 relative to moving web 6 so that reflected light 32 travels in a direction that is parallel to the MD, the cross direction (CD) resolution of sensor 2 is maintained. Although reflected radiation 32 shown in FIG. 1A is depicted as traveling "upstream" in the same machine direction as web 6, this feature is not critical to the sensor's function. In other words, sensor 2 will operate even if web 6 moves in the opposite direction so that the reflected radiation is moving "downstream" relative to the web; the critical feature is that incident radiation 30 that emitted from light source 8 travel along a path that is parallel to that of moving web 6 as reflected radiation 32 moves toward detector 18.

As shown in FIG. 1A, the non-contacting optical sensor 2 measures properties of a layer of material 10 that is coated on reflective laminant substrate 12. It is apparent, that the same sensor 2 can operate to measure layer of material 10 prior to being coated onto the reflective laminant substrate 12. In other words, so long as reflective laminant substrate 12 is underneath layer of material 10 to reflect radiation, sensor 2 will operate.

Figure 1B:
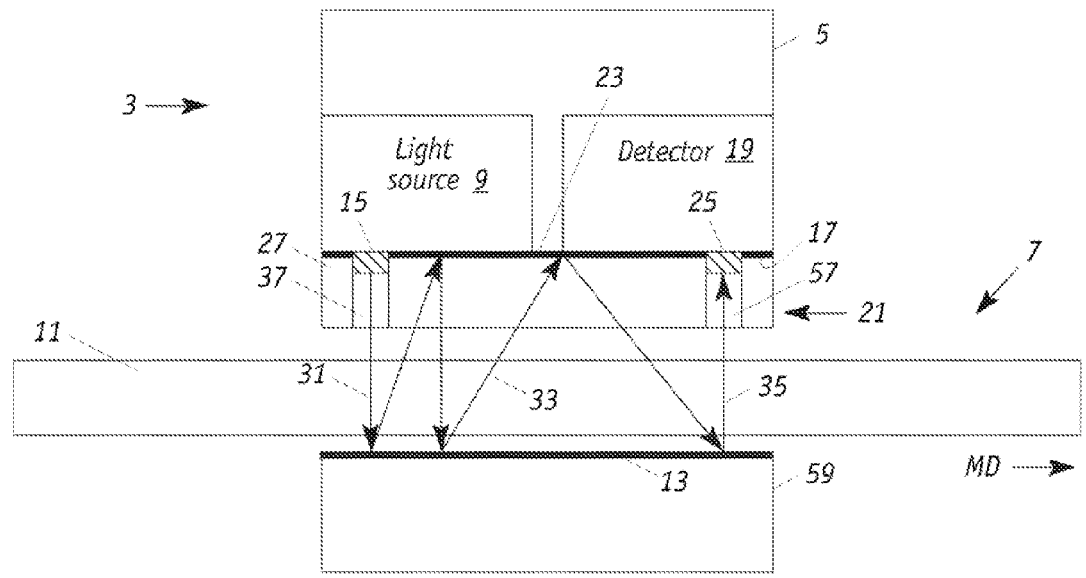

The single-sided infrared sensor of the present invention can also be configured to analyze a layer of material that is not formed on a reflective laminant substrate. This is readily achieved by employing an external reflective member that is positioned adjacent the lower surface of the layer of material. In addition, in a preferred embodiment, the sensor can also include a diffusing element so that light source 9 becomes a diffuse source of illumination. These features are illustrated in the optical sensor 3 as depicted in FIG. 1B, which includes an enclosure or scanner head 5 that houses light source 9 and detector 19 that measures characteristics of a moving web 7 that comprises a layer of material 11 that is transmissive to radiation. A reflective assembly 21, which is secured to the lower surface 23 of head 5, includes a mirror 17 and a diffusing element 27, which can comprise a bulk diffuser.

Sensor 3 further includes a lower scanner head 59 that has a reflective surface 13, such as a specular mirror, which is positioned adjacent to the lower surface of the layer of material 11. The upper and lower scanner heads 5, 59 are aligned so that mirror 17 of the upper scanner head 5 is parallel with and faces reflective surface 13. In addition, the movement of the upper and lower scanner heads 5, 59 in the cross direction is coordinated so that light is reflected between mirror 17 and reflective surface 13 as radiation 33 propagates through layer of material 11. In a preferred embodiment, the lower head 59 is not required and the reflective surface is part of the sheet making machine or part of the scanner. The scanner head 5 can be located such that light is reflecting off an element of the sheet making machine such as a roll. Alternatively, a reflective element such as a foil or a metal plate that spans the full cross-direction width of the layer of material is attached to or is part of the scanner and is positioned adjacent to the lower surface of the layer of material. Apertures 37 and 57 provide access to light source 9 and detector 19, respectively. Lens 15 is positioned to locus a beam of incident radiation 31 through aperture 37 toward moving web 7 and lens 25 is positioned to collect radiation 35 that is reflected from reflective surface 13 through aperture 57. Specifically, incident light 31 from light source 9 is reflected by lower reflective surface 13 and upper mirror 17 multiple times before the light enters receiver 19.

Light diffusing elements that scatter or diffuse light generally function in one of two ways: (a) as a surface light diffusing element utilizing surface roughness to scatter light in a number of directions; or (b) as a bulk light diffusing element with flat outer surfaces and embedded light-scattering elements. The bulk diffuser diffuses the light within the material. Diffusion is achieved by light scattering as it passes though materials with varying indexes of refraction. The term "diffuser" or "diffuser member" means any material that is able to diffuse specular light (light with a primary direction) to a diffuse light (light with random direction). The term "light" means electromagnetic radiation having wavelength in ranges that are suited for measuring properties of a layer material with sensors of the present invention. Infrared and/or near-infrared radiation is particularly suited for measuring physical characteristics of paper and plastic products.

Figure 2A:
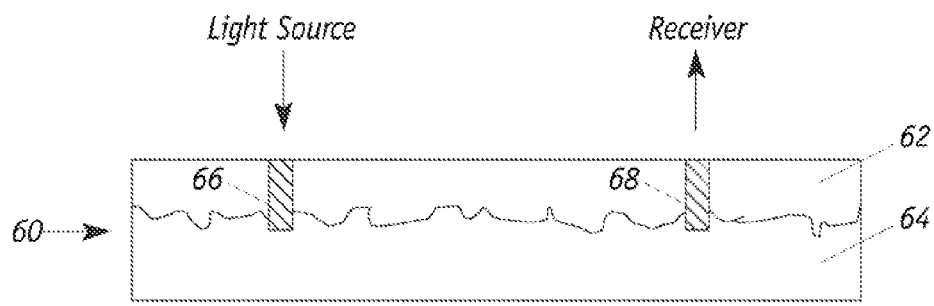
FIGS. 2A, 2B, and 2C illustrate exemplary configurations of reflective assembles with diffuser elements that can be incorporated into single-sided sensors.
Figure 2B:
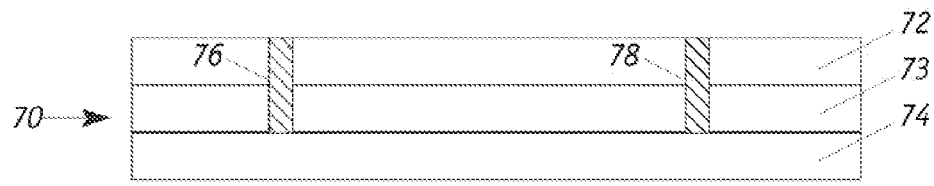
Figure 2C:
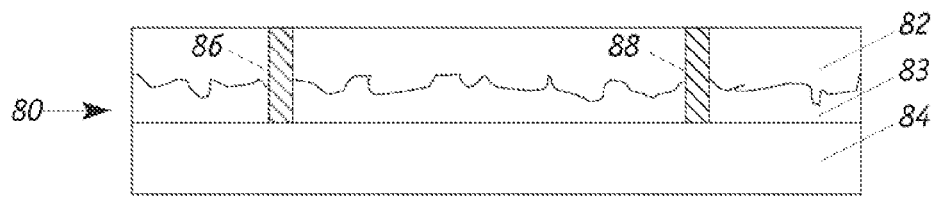

FIGS. 2A, 2B, and 2C illustrate alternative constructions of reflective assemblies with diffuser elements. In FIG. 2A, reflective assembly 60 includes a surface light diffusing element 62 that comprises a reflective material having a rough surface which is shielded by a clear protective layer 64. Surface light diffusing element 62 can be made of any suitable light reflective material such as aluminum, gold, or other metal plate. Light from a light source is channel through surface light diffusing element 62 via aperture or light pipe 66 and light enters the receiver through a corresponding aperture or light pipe 68. Alternatively, surface light diffusing element 62 can be fabricated by stacking a reflective element such as a metal plate or a metallic coating that is deposited on a smooth substrate and a layer of roughened infrared window material. In this embodiment, the infrared window does not need to be protected by a clear layer 64. One embodiment consists of an aluminum coating on a polyimide (KAPTON) film adjacent to a quartz or a calcium fluoride $CaF_2$ window having a roughened surface.

FIG. 2B shows a reflective assembly 70 that includes a mirror 72 with a diffuser element 73 laminated to its lower surface and having a clear protective layer 74 on the exterior. Diffuser element 73 can be made of any suitable bulk diffuser material. In the case where the infrared radiation is employed to measure the properties of the layer of material, preferred diffusing materials include, for example, infrared transmitting materials such as polytetrafluoroethylene (PTFE) that is available as TEFLON or aluminum oxide ($Al_2O_3$). Apertures or light pipes 76, 78 are in communication with light source and light receiver. These light channels can but do not have to extend through diffuser element 73 to clear protective layer 74. The clear protective layer 74 can be an infrared transmitting window made of quartz, sapphire or $CaF_2$.

FIG. 2C shows a reflective assembly 80 that includes a surface light diffusing element 82, a layer of bulk diffuser material 83, and a clear protective layer 84. Apertures or light pipes 86, 88 are in communication with light source and light receiver.

Figure 3:
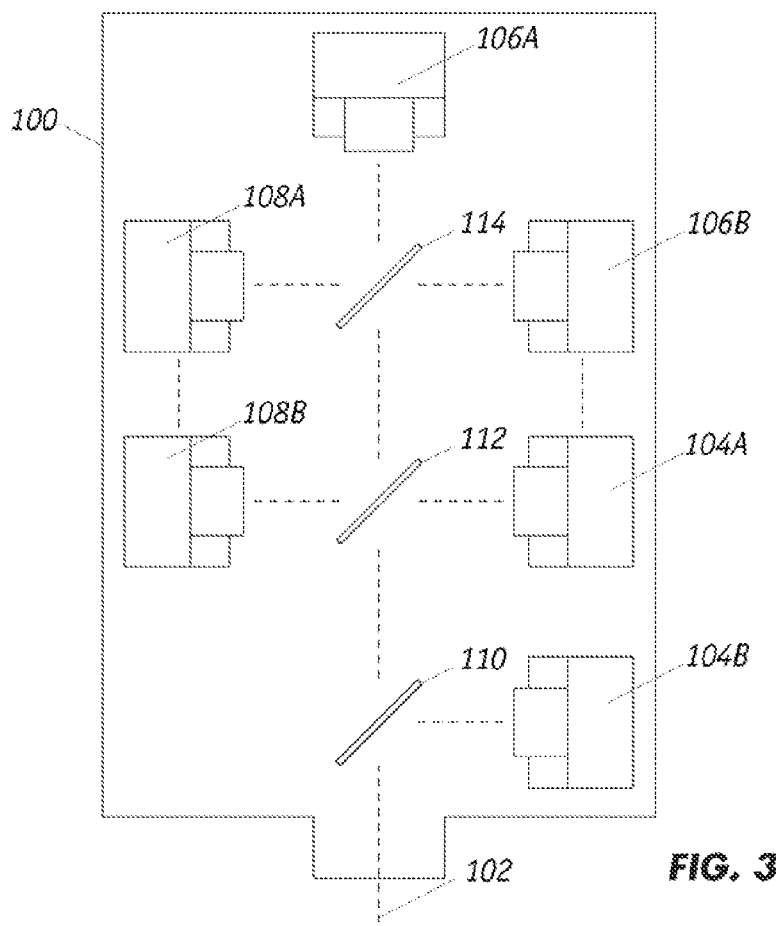
FIGS. 3 and 4 illustrate the light receivers.
Figure 4:
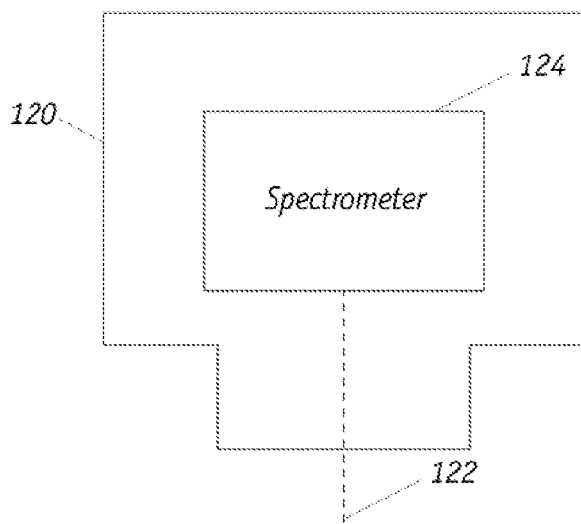

FIG. 3 illustrates a suitable receiver that includes a detector assembly 100 that houses a six-channel sensor for measuring three properties in a layer of material. In this arrangement, there are three measurement filter/detectors 104A, 106A and 108A and three corresponding reference filter/detectors 104B, 106B, and 108B. A separate infrared band pass filter is positioned before each detector: in this fashion, each of the infrared detectors measures the intensity of only the portion of the infrared beam spectrum that falls within the band pass of the associated filter. A broadband infrared source of energy (not shown) directs incident radiation onto the layer of material to be analyzed and reflected radiation 102 is wavelength-analyzed by passing the beam through beam splitters 110, 112, 114 and the appropriate filters to the individual detectors. As is apparent, additional pairs of measure and reference detector/filters can be incorporated as needed. Suitable light sources and associated detector arrangements are described, for instance, in U.S. Pat. Nos. 4,957,770 to Howarth, 7,291,856 to Haran et al., and 7,382,456 to Tixier et al., which are incorporated herein by reference. Alternatively, as shown in FIG. 4, the receiver comprises a detector assembly 120 that employs a spectrometer 124 that analyzes reflected radiation 122.

Figure 5:
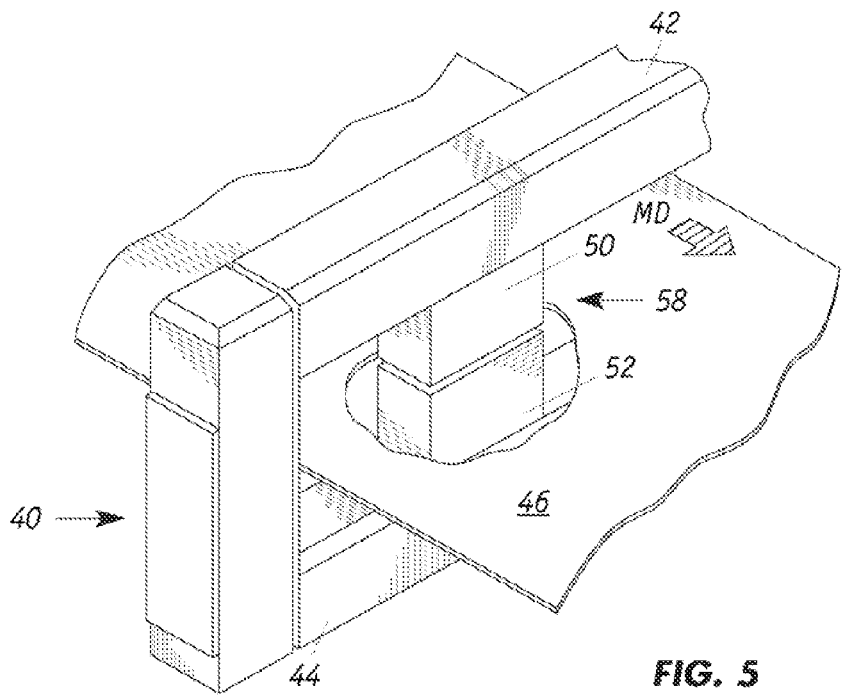
FIG. 5 shows a sheetmaking system implementing the sensor in a dual scanner.

FIG. 5 illustrates one particular implementation of the sensor that is shown in FIG. 1B whereby the sensor is incorporated into a dual head scanner 58 of scanner system 40 that is employed to measure the concentration of polymer in films deposited on a clear substrate in a continuous plastic production process. Upper scanner head 50, which houses the single sided sensor, moves repeatedly back and forth in the CD across the width of the moving sheet 46, which moves in the MD, so that the characteristics of the entire sheet may be measured. Scanner 58 is supported by two transverse beams 42, 44, on which are mounted upper and lower scanning heads 50, 52. The operative faces of the lower and upper scanner heads 50, 52 define a measurement gap that accommodates sheet 46. The lower scanner head 52 may include a sheet stabilization system such as an air-bearing stabilizer (not shown) to maintain the sheet on a consistent plane as it passes through the measurement gap. The movement of the dual scanner heads 50, 52, is synchronized with respect to speed and direction so that they are aligned with each other. The inventive sensor can be employed with any suitable apparatus for continuous production of clear plastic films or plastic films laminated on a metal foil layer. Representative plastic producing devices are further described, for instance, in U.S. Pat. No. 6,793,854 to Kirjavainen, U.S. Pat. No. 6,565,343 to Krycki, U.S. Pat. No. 5,230,923 to Hirokawa et al., U.S. Pat. No. 4,797,246 to Reinke et al., and U.S. Pat. No. 4,311,658 to Nicoll that are incorporated herein by reference.

One technique of monitoring the thickness of a plastic film measures the concentration(s) (weights per unit area, typically measured in grams per square meter, gsm) of the particular polymer(s) that form the film. Multilayer films typically comprise a plurality of layers that are laminated together. Preferably, in the multilayer structure, adjacent layers are formed of different polymer materials. By employing different polymers with different physical properties, the multilayer film may have a combination of physical attributes not present in a single layer film. For example, the multilayer film may be moisture resistant, abrasion resistant, and yet remain pliable. The sensor of the present invention, among other things, is effective in controlling the production of multilayer films to assure that each layer in the film has the proper thickness or weight (gsm) so that the multilayer film has the right combination of properties.

If the density of a particular polymer component in the multilayer film is known the thickness of the film component can be determined. The thickness can be calculated with a computer. Commonly the film thickness is not calculated and the weight (gsm) of the component is all that is required by the user for quality control.

Besides measuring plastic coated products, the inventive sensor with the novel diffusing plate can be readily configured to monitor other substances in coated products by selecting the appropriate reference and measurement wavelength bands. For example, techniques for using infrared radiation to detect silicone, latex, $CaCO_3$, and other materials are described in U.S. Pat. Nos. 6,179,918 to Belotserkovsky, 6,183,561 to Belotserkovsky, and 5,795,394 to Belotserkovsky et al., which are incorporated herein by reference. It is expected that the same reference and measurement wavelength bands can be employed with the inventive sensor.

The foregoing has described the principles, preferred embodiments and modes of operation of the present invention. However, the invention should not be construed as being limited to the particular embodiments discussed. Thus, the above-described embodiments should considered as illustrative rather than restrictive, and it should be appreciated that variations may be made in those embodiments by workers skilled in the art without departing from the scope of the present invention as defined by the following claims.

What is claimed is:

1. An apparatus for sensing a layer of material, with a first surface and a second surface wherein the second surface is coated on a reflective laminant substrate, that comprises:
   a housing having an operative surface;
   a radiation source, disposed within the housing, that directs
      a beam of incident radiation away from the operative
      surface and into the layer of material through the first
      surface;

a radiation receiver, disposed within the housing, that detects at least a portion of a reflected beam that propagates through the layer of material which is transmissive to radiation;

means for reflecting radiation through the layer of material a plurality of times before being detected by the radiation receiver, wherein the means for reflecting radiation comprises a reflective surface that is secured to the operative surface and wherein the layer of material is positioned so that radiation that is transmitted through the layer of material is reflected through the layer of material by the reflective laminant substrate and the reflective surface that face each other with the layer of material being situated in between;

a diffuser element attached to the reflective surface; and clear protective layer on the diffuser element.

2. The apparatus of claim 1 comprising a mirror secured to the operative surface that reflects radiation toward the layer of material.

3. The apparatus of claim 1 wherein the radiation receiver comprises at least one of a plurality of single channel detectors or an optical spectrometer.

4. An apparatus for sensing a layer of material that comprises:

a housing having an operative surface;

a radiation source, disposed within the housing, that directs a beam of incident radiation away from the operative surface and into the layer of material;

a radiation receiver, disposed within the housing, that detects at least a portion of a reflected beam that propagates through the layer of material;

means for reflecting radiation through the layer of material a plurality of times before being detected by the radiation receive; and means for diffusing the reflected beam of radiation such that reflected radiation transmitted through the layer of material is channeled from the radiation source to the radiation receiver wherein the means for diffusing the reflected beam of radiation comprises a diffusing member that has a clear protective layer thereon.

5. The apparatus of claim 4 wherein the diffusing member comprises at least one of a surface-diffusing element or a bulk-diffusing element.

6. The apparatus of claim 5 wherein the surface-diffusing element is formed on a reflective material that is orientated to reflect radiation toward the layer of material.

7. A single-sided infrared sensor, for measuring the thickness or weight of a sheet product moving in the machine direction, that comprises:

a housing supporting a radiation source and a radiation receiver, wherein the radiation source directs a beam of incident infrared radiation into the sheet product which is transmissive to radiation;

reflective means disposed between the radiation source and the radiation receiver for reflecting radiation toward the sheet product such that radiation is reflected through the sheet product a plurality of times before reaching the radiation detector and the radiation propagates through the sheet product in the machine direction wherein the reflective means comprises a first reflective surface and a second reflective surface and the sheet product is positioned between the first and second reflective surfaces; and means for diffusing the reflected radiation.

8. The single-sided infrared sensor of claim 7 wherein the sheet product comprises a layer of material that is formed on a sheet of reflective substrate.

9. The single-sided infrared sensor of claim 7 wherein the housing includes a first radiation channel that is coupled to the radiation source and a second radiation channel that is coupled to the radiation receiver.

10. The single-sided infrared sensor of claim 9 wherein the first radiation channel comprises a first aperture or light pipe and the second radiation channel comprises a second aperture or light pipe.

11. The single-sided infrared sensor of claim 7 wherein the beam of incident infrared radiation is substantially perpendicular to the sheet product.

12. The single-sided infrared sensor of claim 11 comprising a clear protective layer on the means for diffusing the reflected radiation.

13. A single-sided infrared sensor, for measuring the thickness or weight of a sheet product moving in the machine direction, that comprises:

a housing supporting a radiation source and a radiation receiver, wherein the radiation source directs a beam of incident infrared radiation into the sheet product; and reflective means, which includes a reflective surface, disposed between the radiation source and the radiation receiver for reflecting radiation toward the sheet product such that radiation is reflected through the sheet product a plurality of times before reaching the radiation detector and the radiation propagates through the sheet product in the machine direction wherein the housing comprises a first scanner head and the reflective surface is (i) disposed on a second scanner head and wherein the first and second scanner heads move in a synchronized fashion along a cross direction or (ii) a roll or a metallic foil or plate that is mounted between two end supports and spans the entire cross-directional width of the sheet product.

14. A single-sided infrared sensor, for measuring the thickness or weight of a sheet product moving in the machine direction, that comprises:

a housing supporting a radiation source and a radiation receiver, wherein the radiation source directs a beam of incident infrared radiation into the sheet product;

reflective means disposed between the radiation source and the radiation receiver for reflecting radiation toward the sheet product such that radiation is reflected through the sheet product a plurality of times before reaching the radiation detector and the radiation propagates through the sheet product in the machine direction wherein the reflective means includes means for diffusing the reflected beam of radiation such that reflected radiation transmitted through the layer of material is channeled from the radiation source to the radiation receiver; and means for diffusing the reflected radiation.

15. The single-sided infrared sensor of claim 14 wherein the beam of incident infrared radiation is substantially perpendicular to the sheet product.

16. The single-sided infrared sensor of claim 15 comprising a clear protective layer on the means for diffusing the reflected radiation.

17. A method of measuring a characteristic of a layer of material that is moving along a path that comprises the steps of:

(a) directing radiation from a radiation source that is disposed on a first side of the path and into the layer of material wherein the radiation from the radiation source is substantially perpendicular to the layer of material upon incident; and (b) causing radiation to be reflected a plurality of times within the layer of material before being detected by a radiation receiver that is also disposed on the first side of the path by positioning a diffusing element between the radiation source and the layer of material wherein the diffusing element provides a source of illumination and a channel for radiation to propagate until it reaches the radiation receiver.

18. The method of claim 17 wherein the layer of material moves along in a machine direction and the radiation detector is positioned such that the reflected radiation travels through the layer of material in the machine direction.

19. The method of claim 17 wherein the diffusing element has a clear protective layer.

\* \* \* \* \*